United States Patent
Tanaami

(10) Patent No.: US 7,560,270 B2
(45) Date of Patent: Jul. 14, 2009

(54) BIOCHIP CARTRIDGE AND BIOCHIP READER

(75) Inventor: Takeo Tanaami, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 431 days.

(21) Appl. No.: 11/204,016

(22) Filed: Aug. 16, 2005

(65) Prior Publication Data

US 2006/0040379 A1 Feb. 23, 2006

(30) Foreign Application Priority Data

Aug. 18, 2004 (JP) .......................... P.2004-237856

(51) Int. Cl.
*C12M 1/34* (2006.01)
*C12M 1/00* (2006.01)

(52) U.S. Cl. .................................................. 435/287.2
(58) Field of Classification Search ............... 435/287.2
See application file for complete search history.

(56) References Cited

U.S. PATENT DOCUMENTS

| 6,686,582 B1 | 2/2004 | Volcker et al. |
| 2003/0235905 A1* | 12/2003 | Spiecker .................. 435/287.1 |
| 2004/0042017 A1* | 3/2004 | Cohen et al. ................. 356/630 |

FOREIGN PATENT DOCUMENTS

| DE | 198 46 928 A1 | 4/2000 |
| DE | 102 27 962 A1 | 1/2004 |
| JP | 11-173987 A | 7/1999 |
| JP | 2002-207007 A | 7/2002 |
| JP | 2004-138420 A | 5/2004 |
| JP | 2004-156911 A | 6/2004 |
| WO | 99/23474 A1 | 5/1999 |

OTHER PUBLICATIONS

Japanese Office Action issued May 29, 2008.

* cited by examiner

*Primary Examiner*—Walter D Griffin
*Assistant Examiner*—Shanta G Doe
(74) *Attorney, Agent, or Firm*—Sughrue Mion, PLLC

(57) ABSTRACT

A biochip cartridge has a vessel and a lid portion having a plurality of microlenses. A biochip having a plurality of sites is provided in the vessel. The plurality of sites are to be disposed at the same pitches as the microlenses. Excitation light is applied to each of the sites through each microlens corresponding to each site, and fluorescence generated from each site passes through a microlens corresponding to each site.

6 Claims, 4 Drawing Sheets

BIOCHIP CARTRIDGE AND BIOCHIP READER

CROSS-REFERENCE TO RELATED APPLICATIONS

This application is based upon and claims the benefit of priority from the prior Japanese Patent Applications No. 2004-237856 filed on Aug. 18, 2004, the entire contents of which are incorporated herein by reference.

BACKGROUND OF THE INVENTION

1. Field of the Invention

This invention relates to a biochip and a biochip reader for applying a plurality of excitation light beams to a plurality of sites of a biochip at the same time.

2. Description of the Related Art

A biochip reader for applying a plurality of excitation light beams to a plurality of sites of a biochip at the same time and observing a specimen at each site is available. (For example, refer to JP-A-2002-207007.)

FIG. 6 is a drawing to show a configuration example of a biochip reader designed to read image information of a plurality of specimens by a non-scanning method, described in JP-A-2002-207007. In the figure, light from a light source 1 becomes collimated light through a lens 2 and is collected by microlenses MLs of a microlens array MA placed with a spacing equal to a specimen pitch P of a biochip 6. Then, the light becomes collimated light through a lens 3 and is reflected on a dichroic mirror 4 and is formed as an image on the biochip 6 through an object lens 5.

Each spot of the biochip 6 is excited by the collected light, producing fluorescence. The fluorescence passes through the object lens 5, the dichroic mirror 4, and a filter 7 in order and is formed as an image on a photoreceiver (for example, a camera, etc.,) 9 through a lens 8. Thus, a specimen surface image can be provided without light scanning. The image formation spot size through the microlens array MA is made almost equal to specimen size S1, S2, . . .

JP-A-2002-207007 is referred to as a related art.

However, the biochip reader in the related art involves the following problems:

(1) Air is involved in optical system and the amount of light that can be received is limited.
(2) It is difficult to perform alignment between multibeam and site.

SUMMARY OF THE INVENTION

An object of the invention is to provide a biochip cartridge and a biochip reader for increasing the received light amounts and eliminating the need for performing alignment between multibeam and site.

The invention provides a biochip cartridge, having: a vessel; and a lid portion having a plurality of microlenses, wherein a biochip having a plurality of sites is provided in the vessel, the plurality of sites are to be disposed at the same pitches as the microlenses, excitation light is applied to each of the sites through each microlens corresponding to each site, and fluorescence generated from each site passes through a microlens corresponding to each site.

According to the biochip cartridge, fluorescence from each site also passes through the microlens for applying exciting light to the site, and fluorescence generated at a wide divergence angle from the site can be collected efficiently. Thus, an image with large numerical aperture and large light amount can be provided.

In the biochip cartridge, each of the sites may be disposed at a position other than the focal position of the microlens in an optical axis direction of the microlens. In this case, the diameter of the excitation light beam spot becomes large on the site face, and the excitation light is applied to all the site surface.

In the biochip cartridge, each of the sites may be provided in a hollow portion formed by the vessel and the lid portion. In this case, the need for alignment between the microlens and the site as in the related art is eliminated.

In the biochip cartridge, the hollow portion is filled with a liquid. In this case, the microlens may be provided with the effect equivalent to an oil immersion lens or a water immersion lens.

In the biochip cartridge, the sites may be attached to a back surface of the lid portion. In this case, fluorescence can be collected efficiently on the microlenses with no buffer liquid.

The invention also provides a biochip reader, having: the biochip cartridge; an excitation light applying portion which applies an excitation light to the biochip cartridge; and a camera which images fluorescence generated from each site of a biochip; a relay lens which is disposed between the biochip cartridge and the camera, and through which the fluorescence passes.

According to the biochip reader, the biochip reader for producing similar effects to those of the biochip cartridge can be easily provided.

The biochip reader may be a scanless biochip reader.

According to the biochip cartridge and the biochip reader, the following advantages are provided:

(1) Buffer liquid is filled into the hollow portion of the cartridge, whereby a wet optical system equivalent to an oil immersion lens or a water immersion lens can be provided and numerical aperture NA can be taken large, so that a bright image with a large light amount can be easily provided.
(2) In the cartridge, biochip sites are placed for fixture opposed to the microlenses without the need for alignment, so that it is unnecessary to perform alignment between excitation light beam and site in using the biochip reader in the related art. Collimated light of excitation light needs only to be applied to the cartridge.

DETAILED DESCRIPTION OF THE PREFERRED EMBODIMENTS

Figure 1:
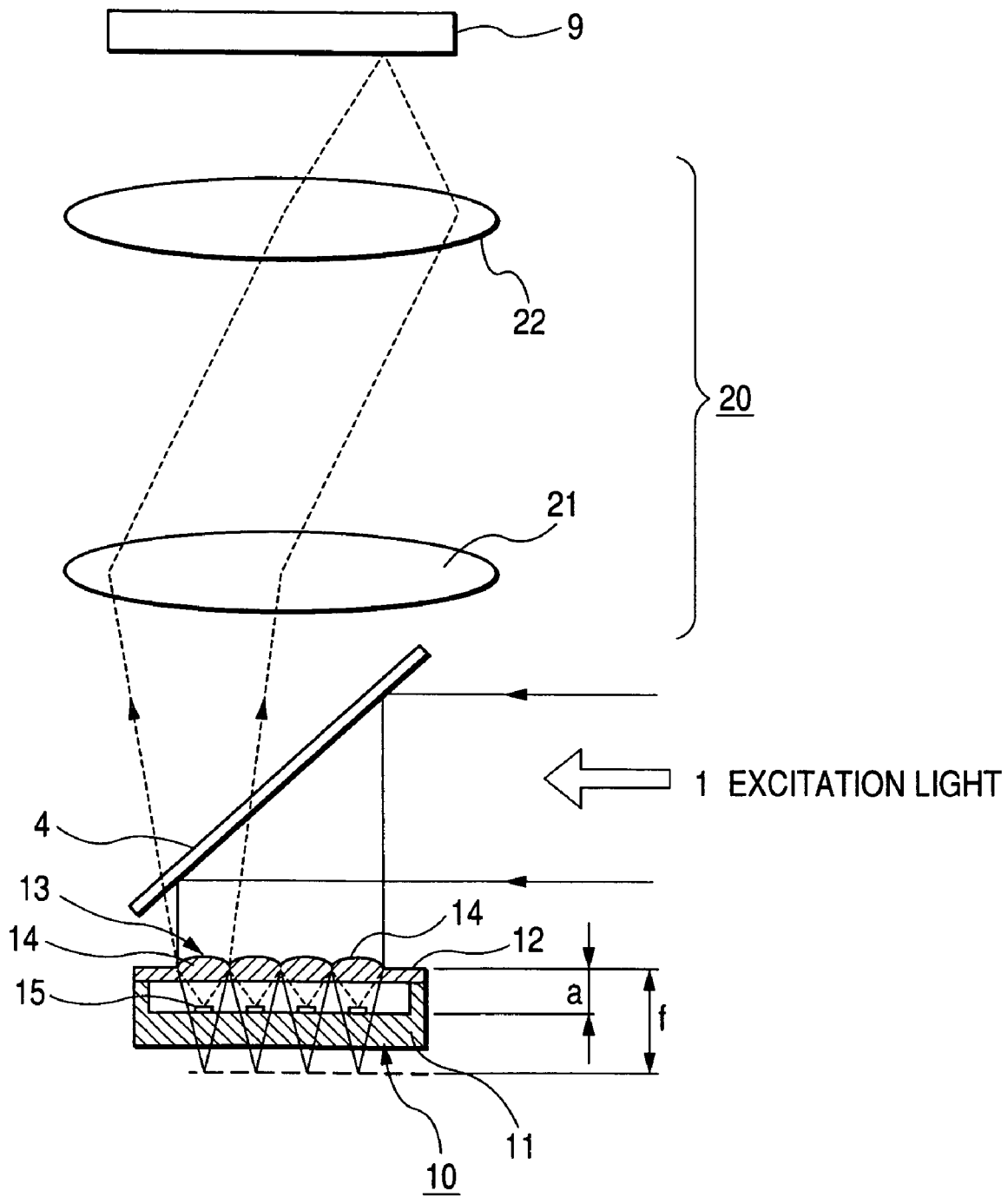
FIG. 1 is a drawing of the configuration of the main part to show an embodiment of a biochip reader according to the invention.
Figure 6:
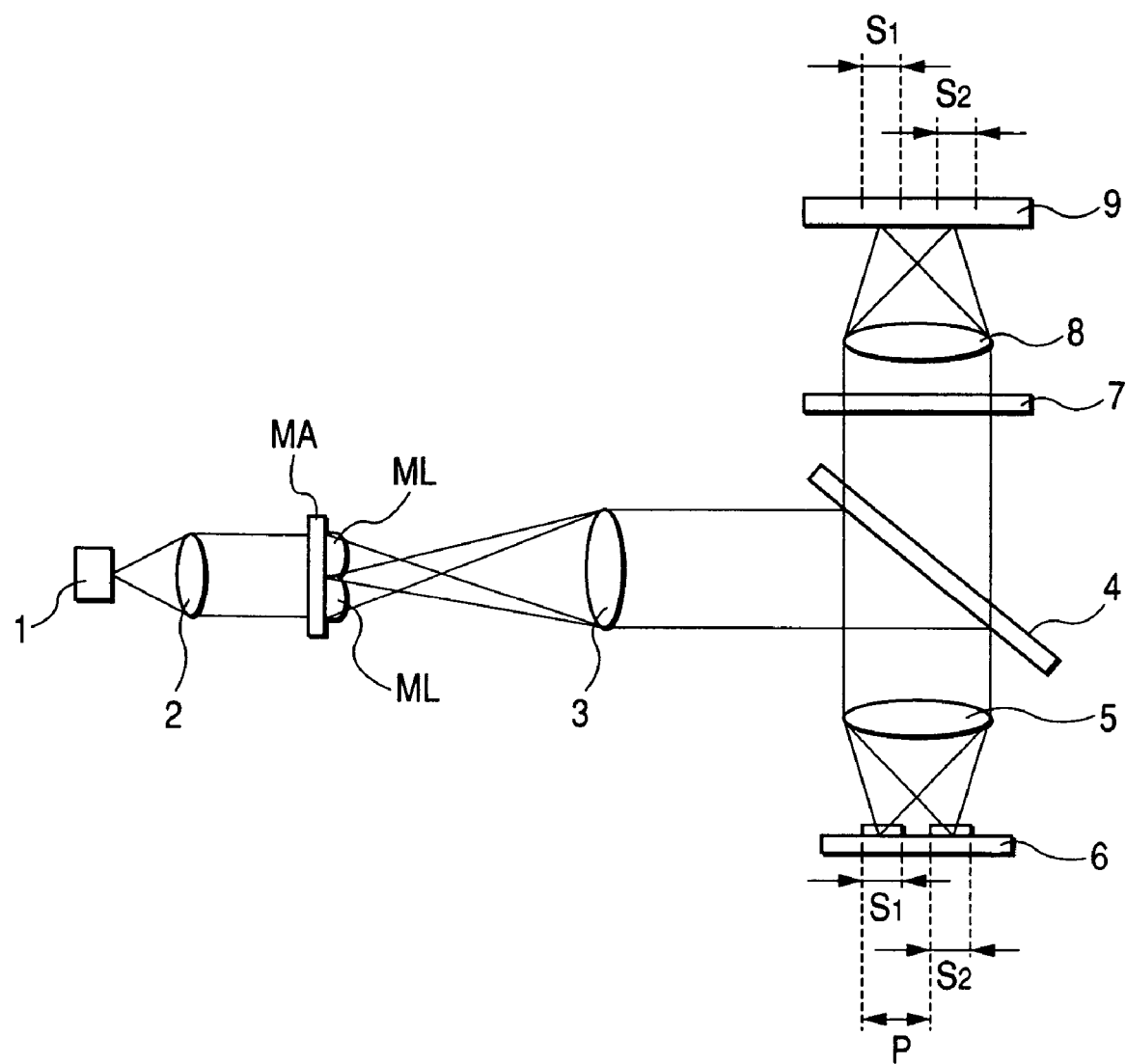
FIG. 6 is a drawing to show a configuration example of a biochip reader in a related art.

Embodiments of the invention will be discussed in detail with the accompanying drawings. FIG. 1 is a drawing of the configuration of the main part to show an embodiment of a scanless (non-optically-scanned) biochip reader according to the invention. Parts identical with those previously described with reference to FIG. 6 are denoted by the same reference numerals in FIG. 1. In FIG. 1, numeral 10 denotes a cartridge and numeral 20 denotes a relay lens having a first lens 21 and a second lens 22.

The cartridge 10 has a box-like vessel 11 and a lid portion 12. The lid portion 12 has a microlens array 13 including a plurality of microlenses 14 for collecting excitation light and fluorescence. The microlens array 13 is formed integrally with the lid portion 12. Sites 15 of a biochip are provided on the internal bottom of the vessel 11. The sites 15 are disposed at the same pitches as the microlenses so that excitation light applied to the site 15 and fluorescence generated from the site 15 passes through the corresponding microlens 14 opposed to the site 15.

A material having good transmittance for excitation light and fluorescence is used for the microlens 14 of the lid portion 12. The vessel 11 of the cartridge 10 is not necessarily formed of the same material as the microlens 14.

The vessel 11 and the lid portion 12 of the cartridge 10 are bonded as they are hermetically sealed at the final stage. Buffer liquid is filled into the internal hollow portion. If buffer liquid is filled, the portion from the microlens 14 to the site 15 becomes a wet optical system equivalent to an oil immersion lens or a water immersion lens. Therefore, numerical aperture NA can be taken large and the light amount increases. For example, if buffer liquid is filled into the part with numerical aperture 0.3 to provide numerical aperture 1.2, the light amount becomes $4^2$=16 times. If buffer liquid is filled into the part with numerical aperture 0.9 to provide numerical aperture 1.2, the light amount becomes $1.3^2$=1.8 times.

The relay lens 20 is made up of the first lens 21 and the second lens 22 and is placed between a dichroic mirror 4 and a camera 9.

FIG. 1 shows only the optical path involved in fluorescence from one site as a representative.

The operation of the described biochip reader is as follows: Collimate light of excitation light 1 is reflected on the dichroic mirror 4 and the reflected collimated light is incident on all of the microlenses 14 at once. The site 15 is placed at a position a before the position of a focal distance f of the microlens 14 (a<f) so that the focus spot of the excitation light beam applied to the site 15 becomes lager than the size of the site 15. Accordingly, the excitation light is applied widely and uniformly to all area of the surface of the site 15 as compared with the case where the site 15 is at the position of the focal distance f.

Other paired microlenses and sites are placed with a similar spacing.

As the excitation light is applied, a fluorescent material of a sample (not shown) on the site 15 is excited and generates fluorescence. This fluorescence goes to the relay lens 20 through the microlens 14 as divergent light rather than collimated light and is formed as an image on the light reception face of the camera 9 through the relay lens 20, as shown in the figure. Similarity also applies to other sites.

According to the configuration, excitation light and fluorescence pass through the same microlens for each site. Since the site 15 is placed close to the microlens 14, the microlens 14 can efficiently collect fluorescence spread at a large divergence angle, and a similar advantage to that provided by using an oil immersion object lens or a water immersion object lens is produced.

Figure 2:
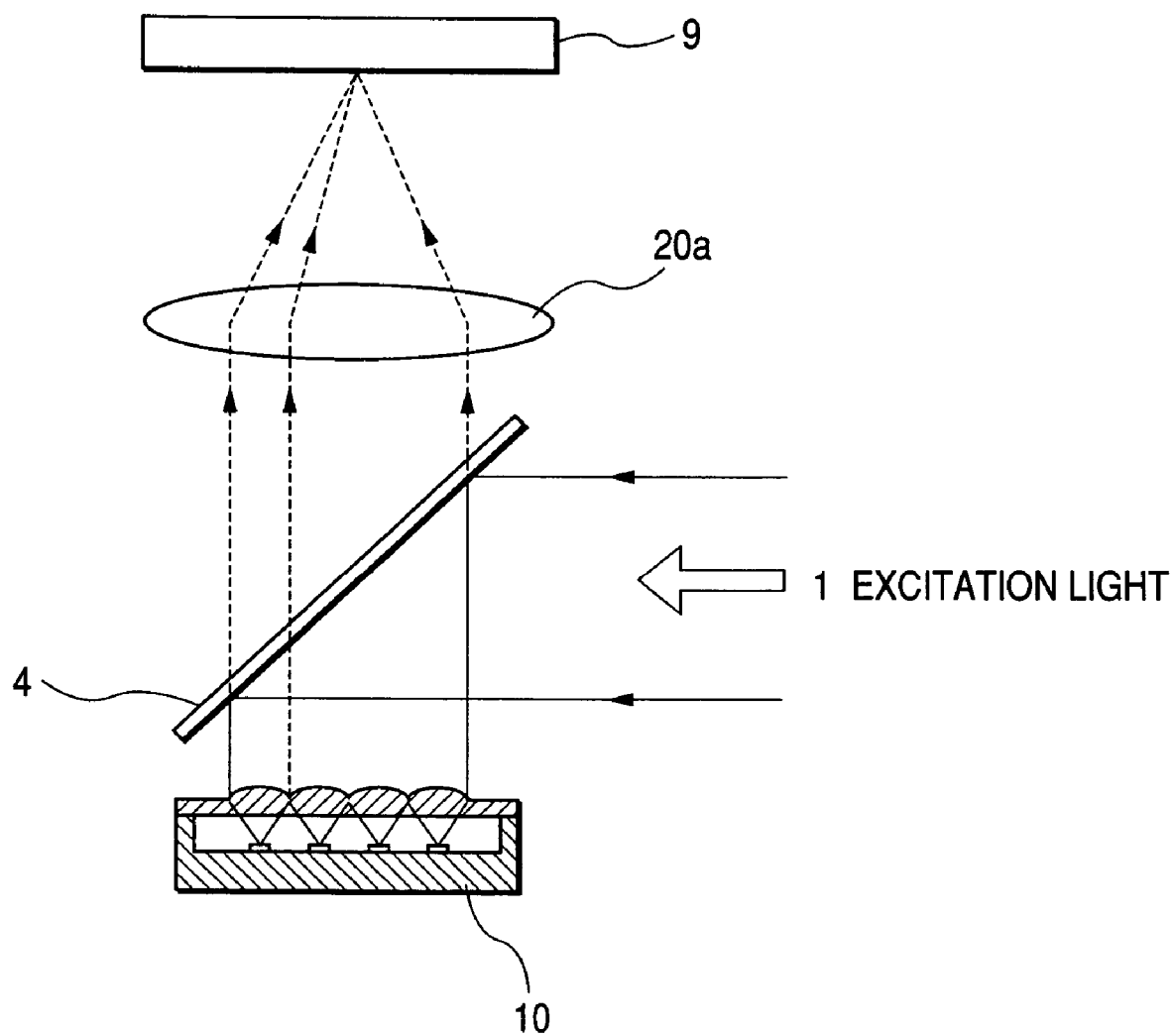
FIG. 2 is a drawing to describe how an image is formed when the site position is focused.

Since the position of the site 15 is shifted from the position of the focal distance f of the microlens 14 on the optical axis, excitation light beam can be applied to all the site surface. If the focus of the microlens 14 is set to the site surface (namely, a=f), the excitation light is applied only to one point on the site and as shown in FIG. 2, return light beams (dashed lines in FIG. 2) become all collimated light through the microlenses 14 and the collimated light (return light) is focused through a lens 20a and is collected only at one point on the camera 9, forming no image; this is a problem. The lens 20a corresponds to the composite lens of the lenses 21 and 22 shown in FIG. 1.

However, such a problem does not occur if a shift is made between the focus position and the site position as in the invention.

Figure 3:
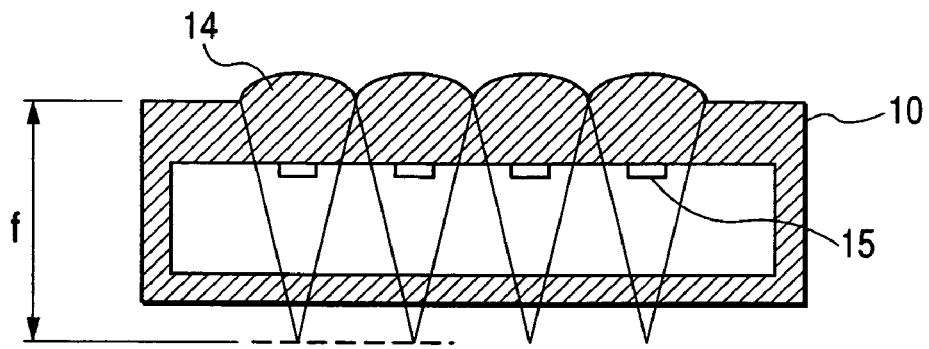
FIG. 3 is a drawing of the configuration of the main part to show another embodiment of the invention.
Figure 4:
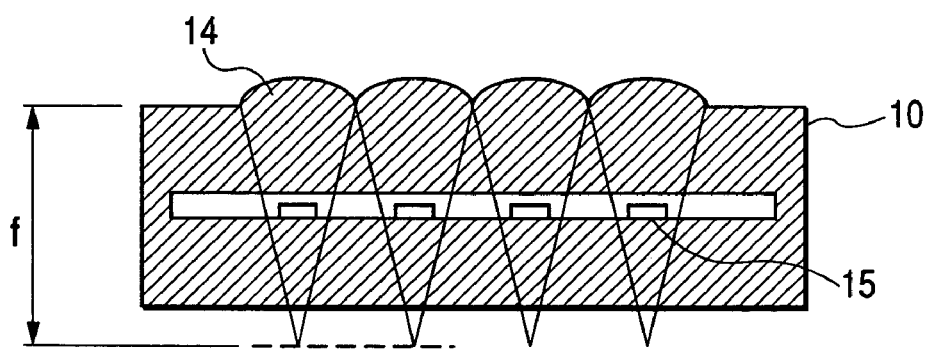
FIG. 4 is a drawing of the configuration of the main part to show still another embodiment of the invention.
Figure 5:
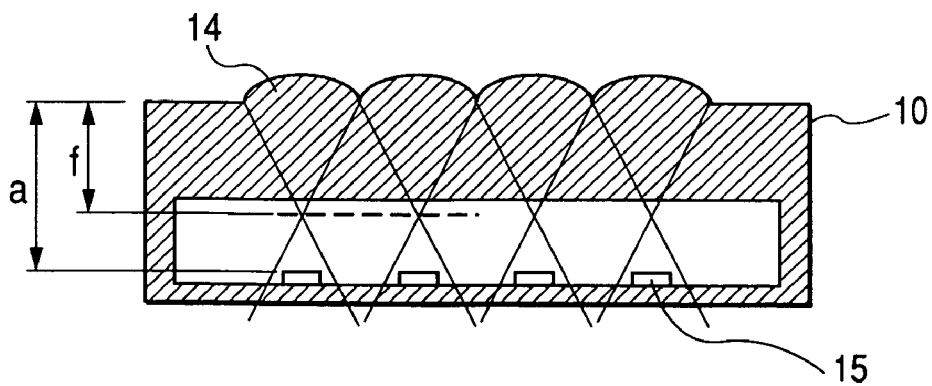
FIG. 5 is a drawing of the configuration of the main part to show still another embodiment of the invention.

The invention is not limited to the above embodiment described above and includes various changes and modifications without departing from the spirit and the scope of the invention. For example, the following embodiments are also included:

(1) Each site 15 may be placed on the back of the substrate where the microlenses 14 are formed, as shown in FIG. 3.
(2) If the hollow portion in the cartridge 10 is narrow, the hollow portion may be empty with no buffer liquid, as shown in FIG. 4.
(3) An excitation light reflection substance such as a metal film may exist on the rear of a site.
(4) The position of the site 15 (distance "a" from the microlens 14) may be at a distance larger than the focal distance f of the microlens 14, as shown in FIG. 5.
(5) The microlenses 14 need not necessarily be formed integrally with the cartridge 10. It may be separated from the cartridge 10 and may exist on the side of the reader (portion made up of the dichroic mirror 4, the relay lens 20, and the camera 9). In this case, however, it becomes necessary to perform alignment between the microlens 14 and the site 15; the effect of increasing brightness can be provided.
(6) As for sites, a biochip having a plurality of sites manufactured outside the cartridge may be inserted into the cartridge for fixture.

What is claimed is:

1. A biochip cartridge, comprising:
  a vessel; and
  a lid portion having a plurality of microlenses,
  wherein a biochip having a plurality of sites is provided in the vessel,
  the plurality of sites are to be disposed at the same pitches as the microlenses,
  excitation light is applied to each of the sites through each microlens corresponding to each site, and
  fluorescence generated from each site passes through a microlens corresponding to each site;
  wherein each of the sites is disposed at a position other than the focal position of the microlens in an optical axis direction of the microlenses, such that each site is placed at a position between the corresponding microlens and the focal position of the microlens.

2. The biochip cartridge according to claim 1,
  wherein each of the sites is provided in a hollow portion formed by the vessel and the lid portion.

3. The biochip cartridge according to claim 2, wherein the hollow portion is filled with a liquid.

4. The biochip cartridge according to claim 1, wherein the sites are attached to a back surface of the lid portion.

5. A biochip reader, comprising:
a biochip cartridge according to claim 1;
an excitation light applying portion which applies an excitation light to the biochip cartridge; and
a camera which images fluorescence generated from each site of a biochip;
a relay lens which is disposed between the biochip cartridge and the camera, and through which the fluorescence passes.

6. The biochip reader according to claim 5, wherein the biochip reader is a scanless biochip reader.

* * * * *